(12) United States Patent
Kuehne et al.

(10) Patent No.: US 10,780,228 B2
(45) Date of Patent: Sep. 22, 2020

(54) PREFILLED CONTAINER SYSTEMS

(71) Applicant: Medline Industries, Inc., Northfield, IL (US)

(72) Inventors: Kelley Kuehne, Williamston, MI (US); John T. Bauer, Williamston, MI (US); Curt Carpenter, Webberville, MI (US); Jessica Leginski, Chicago, IL (US)

(73) Assignee: MEDLINE INDUSTRIES, INC., Northfield, IL (US)

( * ) Notice: Subject to any disclaimer, the term of this patent is extended or adjusted under 35 U.S.C. 154(b) by 0 days.

(21) Appl. No.: 13/804,557

(22) Filed: Mar. 14, 2013

(65) Prior Publication Data

US 2013/0296779 A1    Nov. 7, 2013

Related U.S. Application Data

(60) Provisional application No. 61/643,603, filed on May 7, 2012.

(51) Int. Cl.
*A61M 5/31* (2006.01)
*B65B 55/02* (2006.01)
(Continued)

(52) U.S. Cl.
CPC .............. *A61M 5/3134* (2013.01); *A61J 1/05* (2013.01); *A61M 5/3129* (2013.01); *B65B 3/003* (2013.01); *B65B 55/02* (2013.01); *A61L 2202/182* (2013.01); *A61L 2202/21* (2013.01); *A61L 2202/24* (2013.01); *A61M 5/001* (2013.01); *A61M 5/178* (2013.01);
(Continued)

(58) Field of Classification Search
CPC .......... A61M 5/3134; B65B 55/02; A61J 1/05
USPC ....................................... 604/93.01
See application file for complete search history.

(56) References Cited

U.S. PATENT DOCUMENTS 3,630,665 A    12/1971  Andersen
3,878,664 A     4/1975  Zinke
(Continued)

FOREIGN PATENT DOCUMENTS

EP    0079676    5/1983
EP    1930040    6/2008
(Continued)

OTHER PUBLICATIONS

Cyclo Olefin Polymer (COP) Zeonex; Jun. 2012; pp. 1-15.*
(Continued)

*Primary Examiner* — Kevin Joyner
(74) *Attorney, Agent, or Firm* — Fitch, Even, Tabin & Flannery LLP

(57) ABSTRACT

A syringe assembly may include a plunger having a stopper. A barrel may be configured to receive the plunger at an open first end. A tip cap may be removably attached to the second end and may form a chamber within the barrel between the plunger and tip cap. The chamber may be configured to contain a sterilization sensitive material. The barrel may be formed of a plastic material having a high barrier property configured to create a barrier between the sterilization sensitive material and gases produced for sterilization purposes such that the sterilization sensitive material remains unchanged during a sterilization procedure.

20 Claims, 2 Drawing Sheets

(51) Int. Cl.

| | |
|---|---|
| *A61J 1/05* | (2006.01) |
| *B65B 3/00* | (2006.01) |
| *A61M 5/315* | (2006.01) |
| *A61M 5/00* | (2006.01) |
| *A61M 5/34* | (2006.01) |
| *A61M 5/178* | (2006.01) |

(52) U.S. Cl.
CPC ..... *A61M 5/31501* (2013.01); *A61M 5/31515* (2013.01); *A61M 5/347* (2013.01); *A61M 2005/3104* (2013.01); *A61M 2005/31508* (2013.01)

(56) References Cited

U.S. PATENT DOCUMENTS

| | | | |
|---|---|---|---|
| 3,993,751 | A | 11/1976 | Zinke |
| 4,106,622 | A | 8/1978 | Windischman |
| 4,522,302 | A | 6/1985 | Paikoff |
| 4,635,807 | A | 1/1987 | Knapp |
| 5,061,281 | A | 10/1991 | Mares |
| 5,342,673 | A | 8/1994 | Bowman |
| 5,358,475 | A | 10/1994 | Mares |
| 5,597,530 | A | 1/1997 | Smith |
| 5,620,425 | A | 4/1997 | Heffernan |
| 5,741,236 | A | 4/1998 | Kakiuti |
| 5,803,918 | A * | 9/1998 | Vetter .................. A61M 5/315 604/110 |
| 6,161,364 | A | 12/2000 | Kolberg |
| 6,164,044 | A | 12/2000 | Porfano |
| 6,189,195 | B1 | 2/2001 | Reilly et al. |
| 6,331,174 | B1 | 12/2001 | Reinhard et al. |
| 6,458,095 | B1 * | 10/2002 | Wirt et al. ...................... 604/82 |
| 6,719,733 | B1 | 4/2004 | Heffernan et al. |
| 7,998,120 | B2 | 8/2011 | Sano et al. |
| 2002/0051730 | A1 | 5/2002 | Bodnar |
| 2002/0172615 | A1 | 11/2002 | Woodworth |
| 2003/0034264 | A1 | 2/2003 | Hamai |
| 2003/0159969 | A1 | 8/2003 | McMichael |
| 2004/0187438 | A1 | 9/2004 | Clarke |
| 2005/0075611 | A1 | 4/2005 | Hetzler et al. |
| 2005/0101905 | A1 | 5/2005 | Merry |
| 2005/0268573 | A1 | 12/2005 | Yan |
| 2006/0260967 | A1 | 11/2006 | Clarke |
| 2007/0003584 | A1 | 1/2007 | Anderson |
| 2007/0048251 | A1 | 3/2007 | Arthur |
| 2007/0048337 | A1 | 3/2007 | Arthur |
| 2008/0081763 | A1 | 4/2008 | Swetlin |
| 2009/0145876 | A1 | 6/2009 | Kawamura |
| 2009/0281504 | A1 | 11/2009 | Nanba et al. |
| 2010/0106096 | A1 | 4/2010 | Hirokane et al. |
| 2010/0112063 | A1 | 5/2010 | Figuly |
| 2010/0234810 | A1 | 9/2010 | Arai et al. |
| 2010/0298779 | A1 | 11/2010 | Hetzler et al. |
| 2010/0313962 | A1 | 12/2010 | Bondar |
| 2010/0331864 | A1 | 12/2010 | Shetty |
| 2011/0174647 | A1 * | 7/2011 | Shimazaki .......... A61M 5/3134 206/365 |
| 2011/0276005 | A1 * | 11/2011 | Hioki et al. .................. 604/187 |
| 2012/0035129 | A1 | 2/2012 | Wagman |
| 2012/0093803 | A1 | 4/2012 | Altrichter |
| 2012/0094955 | A1 | 4/2012 | Wagman |
| 2012/0121532 | A1 | 5/2012 | Goessl |
| 2013/0032967 | A1 | 2/2013 | Wang |
| 2013/0103023 | A1 | 4/2013 | Monson |
| 2013/0110025 | A1 | 5/2013 | Donnellan |
| 2013/0280346 | A1 | 10/2013 | Powers |
| 2013/0296779 | A1 | 11/2013 | Kuehne |
| 2014/0004253 | A1 | 1/2014 | Ruane |
| 2014/0262883 | A1 | 9/2014 | Devouassoux |
| 2014/0342954 | A1 | 11/2014 | Ingber |
| 2015/0174338 | A1 | 6/2015 | Takemoto |
| 2015/0306282 | A1 | 10/2015 | Scanlon |
| 2016/0135895 | A1 | 5/2016 | Faasse |
| 2016/0200461 | A1 | 7/2016 | Broadbent |
| 2017/0333641 | A1 | 11/2017 | Bamberg |
| 2017/0349313 | A1 | 12/2017 | Kuehne |
| 2018/0105294 | A1 | 4/2018 | Abboud |

FOREIGN PATENT DOCUMENTS

| | | |
|---|---|---|
| JP | 0394766 A | 4/1991 |
| JP | H0788151 | 4/1995 |
| JP | 2003526438 | 9/2003 |
| JP | 2006271461 | 10/2006 |
| JP | 2007507308 | 3/2007 |
| JP | 2008525136 | 7/2008 |
| JP | 2009207619 A | 9/2009 |
| WO | 2005032627 | 4/2005 |
| WO | 2006029528 | 3/2006 |
| WO | 2007024957 | 3/2007 |
| WO | 2008077155 | 6/2008 |

OTHER PUBLICATIONS

Michael N. Eakins; New Plastics for Old Vials; Jun. 2005; pp. 52-57.*
0.9% Sodium Chloride Injection, USP, Jun. 2014, Hospira Inc. (Year: 2014).
AAM I, AAM I TI R56: 2013 Guidance for the development, validation and routine control of an ethylene oxide sterilization process utilizing flexible bag systems for the sterilization of medical devices, Dec. 27, 2013, Association for the ADvancement of Medical Instrumentation (Year: 2013).
Bateman, Relative Humidity and the Killing of Bacteria, May 10, 1961 (Year: 1961).
Daryl L. Woodman, Determination of Spore Lethality at low Ethylene Oxide Gas Concentrations at Atmospheric Pressure, Jul. 7, 2011, Andersen Scientific Inc. (Year: 2011).
Ernst, Ethylene Oxide Gaseous Sterilization for Industrial Applications, 1972, Duke University Press (Year: 1972).
Federal Register, vol. 43, No. 122, Jun. 23, 1978, pp. 27 47 4-27 480 (Year: 1978).
Food Safety and Inspection Service, Food Safety Information, Oct. 2011, USDA (Year: 2011).
Gisela C.C. Mendes, Ethylene oxide sterilization of medical devices: A review, Nov. 2007, AJIC: American Journal of Infection Control, Federal Register, vol. 43, No. 122 (Year: 2007).
International Search Report and Written Opinion for PCT/US2013/039884, dated Sep. 30, 2013 (18 pages).
International Search Report and Written Opinion from PCT/US17/33719, dated Jul. 20, 2017 (17 pages).
Lucas, Residual Ethylene Oxide in Medical Devices and Device Material, Jan. 8, 2003.
M D+DI, EtO Sterilization: Principles of Process Design, Dec. 1, 1998, Medical Device and Diagnostic Industry, https://www.mddionline.com/eto-sterilization-principles-process-design (Year: 1998).
Moldenhauer, "Chapter 12: Sterlization Processes," Contamination Control in Healthcare Product Manufacturing vol. 2, edited by Madsen and Moldenhauer, PDA-DHI, 2014, pp. 1-79, p. 23 para 3.
Office of Air Quality Planning and Standards, Ethylene Oxide Commercial Sterilization and Fumigation Operations Neshap Implementation Document, Mar. 2004, EPA (Year: 2004).
PCT International Search Report and Written Opinion dated Jul. 20, 2017 for PCT/US17133719.
Wattal et al., "Chapter 10: Decontamination and Sterilization Procedures," Hospital Infection Prevention: Principles I:md Practices, edited by Khardori, Springer, Oct. 30, 2013, pp. 103-120; p. 113 col. 1 para 4.

* cited by examiner

PREFILLED CONTAINER SYSTEMS

CROSS REFERENCE TO RELATED APPLICATION

This application claims priority to U.S. Provisional Patent Application No. 61/643,603, filed May 7, 2012, the contents of which are incorporated by reference in their entirety.

FIELD OF TECHNOLOGY

The present disclosure relates to containers that are at least partially prefilled with material that is sensitive to sterilization techniques including but not limited to ethylene oxide (EtO) sterilization.

BACKGROUND

It is known to prefill containers, including vials and syringes, with material that is sensitive to sterilization techniques. For example, IV flush, drugs, vaccines or other materials may experience a change to their composition or properties when exposed to sterilization. Such changes may include, for example, an undesired shift in pH following EtO sterilization.

Such prefilled containers containing sterilization-sensitive material may be packaged with other materials and/or equipment requiring sterilization. For example, collectively packaged kits such as surgical or procedural kits may include prefilled containers as well as instruments requiring sterilization, among other contents or components necessary to perform a given medical procedure. In such instances where prefilled containers include sterilization-sensitive material and require sterilization, it is known to use glass containers due to the barrier properties of glass.

Conventional solutions may have certain limitations. For example, glass containers may be fragile, may sliver and contaminate the material therein, and may break or chip during shipping and handling. Further, glass is relatively costly to manufacture and transport, and has inherent limitations relating to geometry, size and intricacy of the container.

One method of addressing the known sterilization limits inherent to plastic containers is to attach the non-sterile, prefilled container to the sterile kit post-sterilization; in effect creating a secondary non-sterile kit comprised of a non-sterile prefilled container and a sterile kit. The added step of separately packaging plastic containers may make manufacturing more time consuming and expensive. Separately packaging plastic containers may also reduce the convenience and utility of a surgical kit. Maintaining sterile technique during a procedure becomes more challenging when a separately packaged, non-sterile component must be handled. This may affect the sequence of actions required to complete a given procedure; or, in some cases, the number of physicians needed to complete a procedure.

It is desired to address one or more such limitations experienced with the plastic container systems, packaged kits, and/or methods disclosed herein.

BRIEF DESCRIPTION OF THE D WINGS

DETAILED DESCRIPTION

Figure 1:
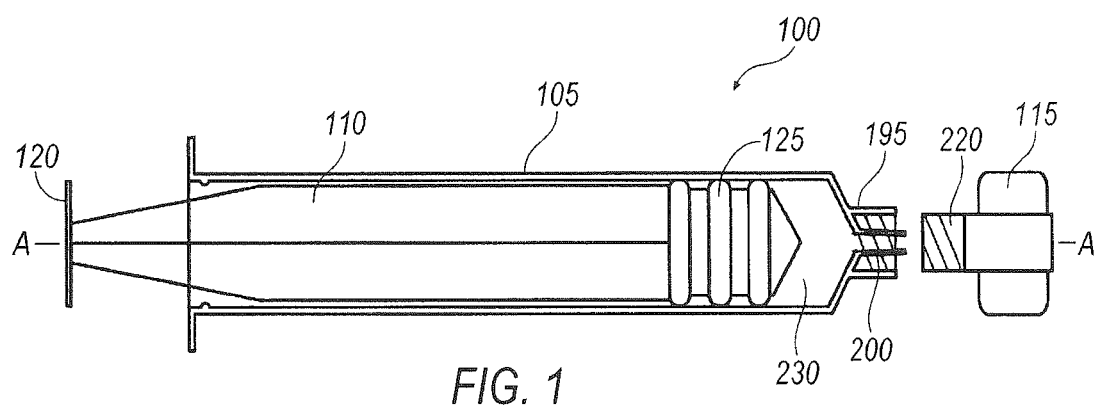
FIG. 1 illustrates a side view of an exemplary syringe assembly.

Referring now to the drawings, illustrative examples are shown in detail. Although the drawings represent certain examples, the drawings are not necessarily to scale and certain features may be exaggerated to better illustrate and explain an innovative aspect of an example. Further, the examples described herein are not intended to be exhaustive or otherwise limiting to the precise form and configuration shown in the drawings and disclosed herein.

A prefilled container system may include a syringe assembly having a barrel, plunger and tip cap. A chamber may be formed within the barrel between the plunger and tip cap and may be configured to hold materials such as sterilization sensitive materials. The syringe assembly may be formed of various materials and/or solutions that permit the syringe assembly to be sterilized and packaged with a surgical kit containing other items necessary to perform a medical procedure. For example, as determined by medical professionals such as surgeons and operating room staff, such kits may be tailored to particular procedures and may include items such as instruments, drugs, antiseptics, dressings that are appropriate and needed for the particular procedure. For convenience, it is preferred that individual items not be separately packaged.

For health and sanitary purposes, it may be desired and necessary that all items within the kit be sterilized and ready for use by the medical professionals. During manufacturing, the items within the kit may be sterilized using terminal sterilization. Terminal sterilization methods may include EtO sterilization, autoclaving, or other methods such as irradiation. In one embodiment, terminal sterilization is used as the sole sterilization step in the assembling and manufacturing of the packaged kits. However, as explained above, the EtO gases used during terminal sterilization may alter the composition of the material within a syringe.

Accordingly, a syringe assembly 100, as shown in FIG. 1, may include a barrel 105, a plunger 110 and a tip cap 115. A chamber 230 may be formed between the tip cap 115 and the plunger 110 within the barrel 105. Any number of solutions (i.e., material) may be included in the chamber 230. In one example, the solution may include an IV flush material such as a saline solution. The solution may include active ingredients such as vaccines, drugs, probiotics, diagnostic compositions, etc. Typically, the chamber contents are a liquid solution that is sterile; either by an aseptic filling process or post filling terminal sterilization. These solutions, when included in a procedural kit, may be affected by the terminal kit sterilization process, such as EtO sterilization as explained above. The kit sterilization is necessary to ensure all the contents of the finished procedural kit are sterile.

The contents of plastic containers, as described above, may be compromised during the kit sterilization process and, therefore, the solution contained therein may be affected and considered "sterilization sensitive." For example, EtO sterilization may include subjecting the filled syringe assembly 100 to EtO gas. The gas may kill any micro-organisms and ensure that the assembly 100 is sterilized prior to use. The EtO gases may alter the composition of the sterilization sensitive solution. However, as explained below, the syringe assembly 100 provides a chamber 230 capable of creating an effective barrier between the sterilization gases and the solution so that the solution remains substantially unchanged within the chamber 230 during sterilization. Thus, the solution remains within acceptable specifications for the manufacture, sale, and use of the device. For example, if the solution is a drug and it remains substantially unchanged after exposure to sterilization, then the device and solution still meets the regulatory requirements for the manufacture, sale, and use of that drug.

Figure 2:
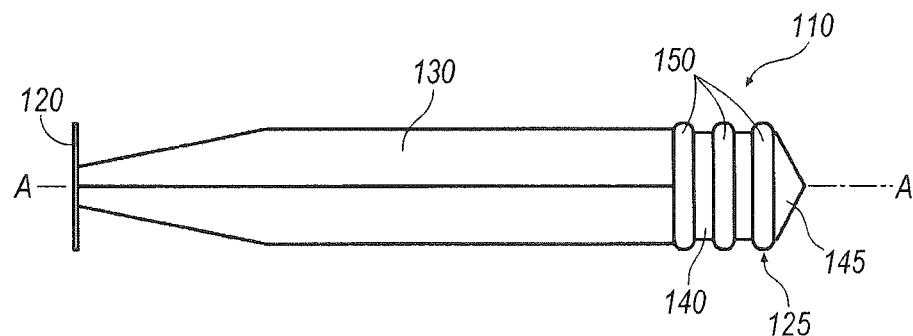
FIG. 2 illustrates a side view of an exemplary plunger assembly for use with the syringe assembly of FIG. 1.
Figure 3:
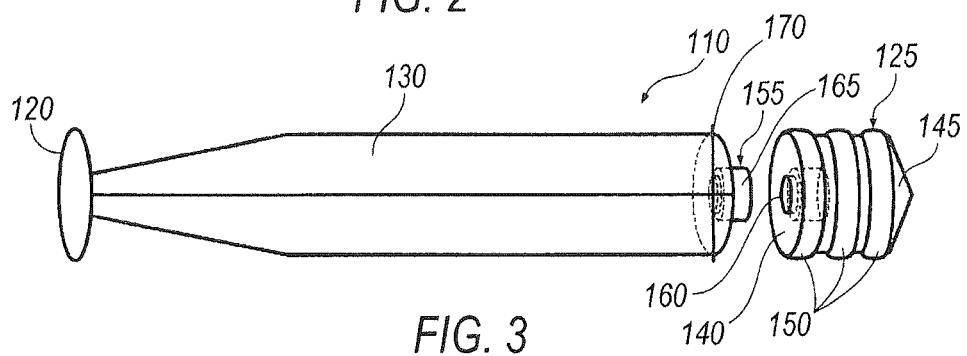
FIG. 3 illustrates an exploded view of the exemplary plunger assembly of FIG. 2.

The plunger 110, as shown in FIGS. 1-3, may include a plunger body 130 extending along the axis A and having a base 120 at one end and a stopper 125 at the opposite end of the plunger body 130. The stopper 125 may include a cylindrical portion 140 and an end portion 145, which may have a conical shape. The cylindrical portion 140 may include at least one wiper 150 extending radially around the cylindrical portion 140.

The stopper 125 may be connected to the plunger body 130 via an attachment mechanism 155. In one exemplary arrangement, the attachment mechanism 155, as shown in FIG. 3, may include a male and female connection mechanism, whereby the stopper 125 may define an opening 160 configured to receive a post 165 extending outwardly along the axis A of the plunger body 130 so as to frictionally engage the stopper 125. However, it is understood that the attachment mechanism 155 is not limited to the configuration shown in FIGS. 1-3. Indeed, the attachment mechanism 155 may also include several other mechanisms for securing the stopper 125 to the plunger body 130. For example, an adhesive such as glue may be used, as well as tape, including two sided tape. Additionally or alternatively other mechanisms may be used such as a screw mechanism, hook and eye mechanism, etc.

The stopper 125 may have relatively a stiff elastic modulus and be formed from one or more materials, including high barrier thermoplastic elastomers. Exemplary elastomers may include, but are not limited to, butyl rubber. The stopper 125 may also be coated for increased barrier properties. The plunger body 130 may include one or more plastic materials. For example, suitable plastics may include injection moldable cyclic olefin polymer (COP) or cyclic olefin copolymer (COC). The base 120 of the plunger 110 may be formed so as to be co-extensive with the plunger body 130 and thus include similar materials. During sterilization, the base 120, and at least a portion of the plunger body 130 may be exposed to EtO gases. However, the plunger body 130 and base 120 may not come into contact with the sterilization sensitive material within the chamber 230. Thus, at least one of the base 120 and plunger body 130 may be formed of less expensive plastics such as polypropylene or polycarbonate.

Figure 4:
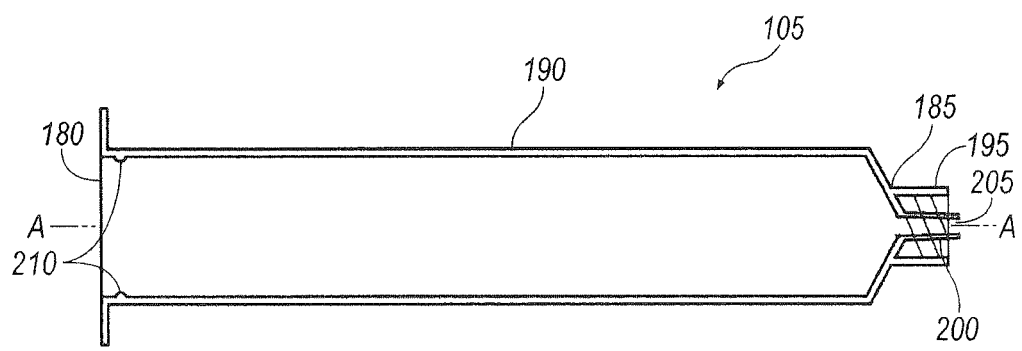
FIG. 4 illustrates a side view of a barrel of the exemplary syringe assembly of FIG. 1.

The barrel 105, as shown in FIGS. 1 and 4, includes a first end 180, a second end 185 and a barrel body 190 extending therebetween. The barrel body 190 may form a cylindrical shape extending along the axis A. The first end 180 may be an open end configured to receive the plunger 110. The second end 185 may include a barrel neck 195. In one exemplary arrangement, the neck 195 may include a male luer 200 defining an opening 205.

The barrel 105 may also include a mechanical engagement system, or barrel flange 210, extending radially inwardly of an inner surface of the barrel 105 adjacent the first end 180. During EtO sterilization, a pressure differential may be created within the barrel 105. This differential may apply a force against the plunger 110, attempting to force the plunger 110 out of the barrel 105. The barrel flange 210 may be configured to engage the outer periphery of a plunger flange 170 and/or the wipers 150 of the stopper 125 to prevent the plunger 110 from expulsion from the barrel 105. In one exemplary method, an air bubble is intentionally left within the barrel after filling the chamber 230 with solution. The air bubble facilitates a large pressure differential and outward force of the plunger 110 during sterilization. As this outward force increases, so does the contact pressure between at least one of the stopper 125 and the plunger flange 170 and the barrel flange 210, increasing effectiveness of the mechanical seal to isolate the contained solution. In another exemplary method, the chamber 230 is free of air bubbles. Other exemplary mechanical engagements may include one or more protrusions on an inner surface of the barrel 105 that are sufficient to prevent expulsion of the plunger 115.

The barrel 105 may include one or more plastic materials. Barrel 105 composition may include COP and/or COC materials. These polymers may be very similar to glass having high gas impermeability, high moisture barrier and low absorption rate properties. The barrel 105 may be coated with materials for increased barrier properties, such as silicone dioxide or aluminum dioxide. In another embodiment, the barrel 105 may be uncoated. Additionally or alternatively, the barrel 105 may be formed from materials having high clarity so that contents of the barrel may be visibly inspected. The barrel 105 may also be formed from materials having at least one of low water vapor permeability (in one example, less than about 0.5 $g \cdot mm/m^2 \cdot d$ to minimize moisture transmission across walls of the container), low oxygen permeability (in one example, less than about 500 $cm^3 \cdot mm/m^2 \cdot d \cdot bar$ to minimize gas transmission across walls of the container), high heat resistance to withstand temperatures of autoclaving (in one example, the heat resistance is effective to standard autoclaving temperatures), and minimal leaching, elution, extraction, absorption or adsorption.

The barrel 105 may be configured to receive the plunger 110 at the barrel first end 180. The stopper 125 of the plunger 110 may be inserted at the first end 180. The stopper 125, along with the tip cap 115, may be configured to create the chamber 230 within the barrel 105. As explained above, the stopper 125 may have a relatively stiff elastic modulus and the wipers 150 may create a mating surface with the inside of the barrel 105. Thus, the stopper 125 may permit the plunger 110 to move along axis A within the barrel 105 and also create a seal within the barrel 105 to prevent any material from leaving the chamber 230. Moreover, the mating conical surfaces between the barrel 105 and the stopper 125 may also serve to prevent blood uptake after the prefilled syringe has been administered to a patient by preventing the plunger assembly 110 from recoiling upward after administration.

Referring again to FIG. 1, the tip cap 115 may include a female luer 220 configured to receive a mating male luer 200 extending from the barrel 105. The tip cap 115 may be configured to seal the syringe assembly 100 to assist in creating the chamber 230 within the barrel 105. As explained, the chamber 230 may be configured to hold the sterilization-sensitive material. Thus, a portion of the tip cap 115 may come in contact with the material during sterilization, shipping and storage of the syringe. In instances where a syringe assembly 100 is included in a package such as a surgical kit, a needle for insertion into the barrel neck 195 may also be included in the kit.

The tip cap 115 may be made of any number of materials. Exemplary materials may include polycarbonates that possess adequate barrier properties. For example, plastics such as polypropylene coated with a high-barrier material (e.g., butyl rubber) on at least a portion of the tip cap 115 may be used. The surface area of the tip cap 115 exposed to the material in the chamber 230 is relatively small compared to that of the barrel 105 and stopper 125. Thus, the portion exposed to the material may be coated, while the remaining portions of the tip cap 115 may not.

Figure 5:
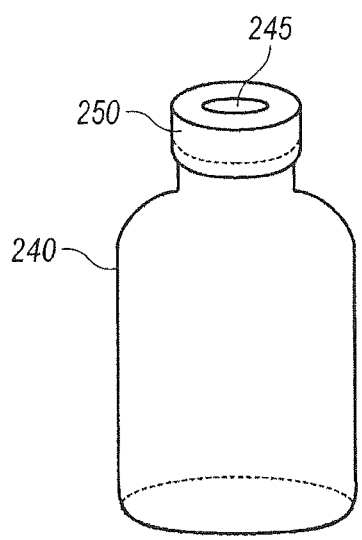
FIG. 5 illustrates a side view of an exemplary vial.

FIG. 5 shows an exemplary vial 240 including a stopper 245 and a cap 250. The vial 240 may be formed from COC or COP and the stopper 245 may include a region formed of a thermoplastic elastomer such as a butyl rubber. The stopper 245 may be fitted within a neck of the vial 240. The cap 250 may surround the top of the vial 240. The vial 240 may include sterilization sensitive material, similar to the syringe assembly 100 above. During sterilization, pressure may build within the vial and the cap 250 may be configured to abut at least a portion of the stopper 245 at the top of the vial to prevent the stopper 245 from being ejected from the vial 240 during pressure increases.

As explained, the outside of the syringe assembly 100 and/or the vial 240 may be sterilized along with the other items within a surgical kit via a variety of sterilization techniques such as EtO sterilization and/or autoclaving. Prior to sterilization, the separate components of the syringe assembly 100 and the vial 240 (e.g., the barrel 105, plunger 110, tip cap 115, etc.) may be manufactured in a clean room environment. Additionally or alternatively, each component may be sterilized prior to assembly. Upon partial assembly of the components, the chamber 230 may be filled with the material. In one example, the stopper 125 of the plunger 110 may be inserted at the first end 180 of the barrel 105 and prior to attaching the tip cap 115 to the barrel neck 195, the material may be filled at the opening 205. The tip cap 115 may then be attached to the barrel 105 at the barrel neck 195, thus sealing the material within the chamber 230. In another example, the tip cap 115 may first be connected to the barrel neck 195 via the luer fitting and the material may be filled at the first end 180 prior to the plunger 110 being inserted into the barrel 105. Once the chamber 230 has been filled, and the plunger 110 inserted, the syringe assembly 100 may be sterilized. For example, the assembly 100 may be placed in an autoclave. By subjecting the syringe assembly 100 to highly saturated steam, the exterior and interior of the components may be sterilized. Once the syringe assembly 100 is removed from the autoclave, the outside of the assembly 100 may become non-sterile; however, the fluid and fluid path remain sterile. The syringe assembly 100 may then be combined with the remaining kit contents. The entire kit may then be sterilized via EtO sterilization. Thus, the outside of the assembly 100 is sterilized and packaged with the rest of the kit items. Due to the specific properties of the barrel 105, plunger 110, stopper 125, and tip cap 115, the material within the chamber 230 is not altered or affected by the sterilization process.

Advantageously, prefilled container systems may be packaged together with other materials requiring terminal sterilization as part of the manufacturing process and need not be separately packaged with materials having high barrier properties such as sealed, foil wrapping.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A pre-filled and pre-sterilized syringe assembly, comprising:
   a plunger including a stopper;
   a barrel formed of a plastic material and having an open first end and an opposite and second end, wherein the open first end is configured to receive the plunger, wherein the barrel is an uncoated barrel such that the EtO-sterilization sensitive material is in contact with the plastic material;
   a tip cap removably attached to the second end, wherein a chamber is formed within at least a portion of the barrel between the stopper and the tip cap, the chamber contains an EtO-sterilization sensitive material, and wherein the tip cap includes a first portion that comes into contact with the EtO-sterilization sensitive material and that is constructed of butyl rubber, and a second portion that does not come into contact with the EtO-sterilization sensitive material, the second portion constructed of a plastic;
   wherein the portion of the barrel and the EtO-sterilization sensitive material contained therein form an EtO-sterilized syringe assembly portion subjected to an EtO sterilization procedure, and wherein the plastic material of the barrel has a barrier property that cooperates with the tip cap to create a barrier between the EtO-sterilization sensitive material and gases produced for sterilization purposes such that the EtO-sterilization sensitive material disposed within the portion of the barrel remains unchanged after being subjected to the EtO sterilization procedure.

2. The syringe assembly of claim 1, wherein the plastic material having a high barrier property includes at least one of a cyclic olefin polymer (COP) and a cyclic olefin copolymer (COC).

3. The syringe assembly of claim 1, wherein the stopper is formed of a high barrier thermoplastic elastomer configured to create a barrier between the EtO-sterilization sensitive material and the gases produced for sterilization.

4. The syringe assembly of claim 1, wherein the stopper includes at least one wiper extending radially outwardly and configured to engage an inside surface of the barrel creating a leak free mechanical engagement.

5. The syringe assembly of claim 4, wherein the plunger includes a plunger flange configured to abut the at least one wiper to prevent expulsion of the plunger from the barrel.

6. The syringe assembly of claim 5, further comprising a barrel flange extending radially inwardly of an inner surface of the barrel, adjacent the open first end, wherein the barrel flange is configured to engage the plunger flange to prevent the plunger from exiting the barrel.

7. The syringe assembly of claim 1 wherein an external surface of the barrel about the chamber is an EtO-sterilized external surface.

8. A packaged kit, comprising:
   an EtO-gas-exposed plastic container system having a plunger and a barrel configured to receive the plunger, wherein the plunger includes a stopper and the barrel is configured to receive the plunger at an open first end;
   the container system further including a tip cap removably attached to a second end of the barrel, the tip cap including a butyl rubber portion and a plastic portion adjacent to the butyl rubber portion, wherein a chamber is formed within the barrel between the stopper and the butyl rubber portion of the tip cap;
   wherein the chamber is prefilled before EtO-gas sterilization such that it contains an EtO-sterilization sensitive material that is subjected to an EtO sterilization procedure while disposed within the chamber, and
   further wherein the butyl rubber portion of the tip cap comes into contact with the EtO-sterilization sensitive material and the plastic portion does not come into contact with the EtO-sterilization sensitive material, and wherein the barrel is formed of a plastic material having a barrier property that cooperates with the tip cap to create a barrier between the EtO-sterilization sensitive material and gases produced for sterilization purposes such that the EtO-sterilization sensitive material remains unchanged after the EtO sterilization procedure, wherein the barrel is an uncoated barrel such that the EtO-sterilization sensitive material is in contact with the plastic material.

9. The packaged kit of claim 8, wherein the plastic material having a high barrier property includes at least one of a cyclic olefin polymer (COP) and a cyclic olefin copolymer (COC).

10. The packaged kit of claim 8, wherein the stopper includes at least one wiper extending radially outwardly and configured to create a mating surface with the inside of the barrel creating a leak free mechanical engagement.

11. The packaged kit of claim 10, wherein the plunger includes a plunger flange configured to abut the at least one wiper to prevent expulsion of the plunger from the barrel.

12. The packaged kit of claim 8, wherein the EtO-sterilization sensitive material is subjected to both the EtO sterilization procedure and autoclaving.

13. The packaged kit of claim 8, further comprising a vial configured to contain a vial EtO-sterilization sensitive material and having a high barrier property configured to create a barrier between the vial EtO-sterilization sensitive material and the gases produced for sterilization purposes such that the vial EtO-sterilization sensitive material remains unchanged during a sterilization procedure.

14. The packaged kit of claim 8 wherein an external surface of the barrel about the chamber is an EtO-sterilized external surface.

15. A syringe assembly comprising:
   a plunger including a stopper;
   a barrel formed of a plastic material and having a first end and a second end opposite the first end, wherein the first end is configured to receive the plunger;
   a tip cap removably attached to the second end, the tip cap formed of discrete materials including a first material at a first surface area of the tip cap and a second material at a second surface area of the tip cap, the second material being different than the first material, wherein the stopper, barrel, and first surface area of the tip cap cooperate to form a chamber within the syringe assembly, and wherein the second material is not exposed to the chamber;
   an EtO-sterilization sensitive material disposed within the chamber and in contact with the first material and not in contact with the second material, wherein the barrel is an uncoated barrel.

16. The syringe assembly of claim 15 wherein the first material is butyl rubber that is in contact with the EtO-sterilization sensitive material and wherein the second material is a plastic that is not in contact with the EtO-sterilization sensitive material.

17. The syringe assembly of claim 15 wherein the second material is coated with the first material.

18. The syringe assembly of claim 15 wherein the EtO-sterilization sensitive material is in contact with the plastic material.

19. The syringe assembly of claim 15 wherein the barrel is free of a silicone material.

20. A pre-filled and pre-sterilized syringe assembly, comprising:
   a plunger including a stopper;
   a barrel formed of a plastic material and having an open first end and an opposite and second end, wherein the barrel is an uncoated barrel such that the barrel is free of a silicone material, wherein the open first end is configured to receive the plunger; and
   a tip cap removably attached to the second end, wherein a chamber is formed within at least a barrel portion between the stopper and the tip cap, the chamber contains an EtO-sterilization sensitive material that is in contact with the barrel portion;
   wherein the plastic material of the barrel has a barrier property that cooperates with the tip cap to create a barrier between the EtO-sterilization sensitive material and gases produced for sterilization purposes such that the EtO-sterilization sensitive material disposed within the barrel portion remains unchanged after being subjected to the EtO sterilization procedure.

* * * * *